United States Patent [19]

Fish, Jr. et al.

[11] Patent Number: 5,354,616
[45] Date of Patent: * Oct. 11, 1994

[54] FISHING LINES AND RELATED PRODUCTS

[75] Inventors: Robert B. Fish, Jr., Parkersburg, W. Va.; Francis G. Gallagher, Wilmington, Del.; James M. McKenna, Hockessin, Del.; Raymond F. Tietz, Wilmington, Del.

[73] Assignee: E. I. Du Pont de Nemours and Company, Wilmington, Del.

[*] Notice: The portion of the term of this patent subsequent to Oct. 1, 2008 has been disclaimed.

[21] Appl. No.: 977,650

[22] Filed: Nov. 16, 1992

Related U.S. Application Data

[63] Continuation-in-part of Ser. No. 834,796, Feb. 13, 1992, which is a continuation-in-part of Ser. No. 645,849, Jan. 25, 1991, Pat. No. 5,097,004, which is a continuation-in-part of Ser. No. 522,134, May 11, 1990, Pat. No. 5,053,482.

[51] Int. Cl.$^5$ .................. D02G 3/00; A01K 91/00
[52] U.S. Cl. .................... 428/373; 428/364; 428/375; 428/395; 43/44.98; 528/274
[58] Field of Search ............. 428/375, 373, 395, 364; 43/44.98; 528/274

[56] References Cited

U.S. PATENT DOCUMENTS

| 3,651,014 | 3/1972 | Witsiepe | 528/274 |
| 3,763,109 | 10/1973 | Witsiepe | 528/274 |
| 4,297,413 | 10/1981 | Sasaki et al. | 428/395 |
| 4,459,337 | 7/1984 | Hansen | 428/395 |
| 4,584,240 | 4/1986 | Herbert et al. | 428/373 |
| 5,053,428 | 10/1991 | Tietz | 528/272 |
| 5,097,004 | 3/1992 | Gallagher et al. | 528/272 |

FOREIGN PATENT DOCUMENTS

| 427496 | 5/1991 | European Pat. Off. | 43/44.98 |
| 404108331 | 4/1992 | Japan | 43/44.98 |

Primary Examiner—Patrick J. Ryan
Assistant Examiner—J. M. Gray

[57] ABSTRACT

Novel fishing lines, and related products, especially monofilamentary products, of polyesters that are biodegradable and disintegrate, when immersed over a period of weeks or months in water, to avoid residues thereof obstructing the aqueous environment, but are storage-stable, i.e.. do not disintegrate while being stored in air, before such lengthy immersion.

5 Claims, No Drawings

FISHING LINES AND RELATED PRODUCTS

CROSS REFERENCE TO RELATED APPLICATIONS

This application is a continuation-in-part of application Ser. No. 07/834,796, filed Feb. 13, 1992, being a continuation-in-part of application Ser. No. 07/645,849, filed Jan. 25, 1991, now U.S. Pat. No. 5,097,004, being a continuation-in-part of application Ser. No. 07/522,134, filed May 11, 1990, now U.S. Pat. No. 5,053,482.

FIELD OF THE INVENTION

This invention relates to fishing lines, sometimes referred to as fishlines, including long line fishing lines and including related products, such as netting products for fishing, and is more particularly concerned with such lines as are novel and are degradable, advantageously, when immersed in water.

BACKGROUND

Nylon (i.e., polyamide) oriented monofilament has increasingly found acceptance as a preferred material for commercial fishlines, as discussed in U.S. Pat. Nos 4,459,337 (Hansen) and 4,584,240 (Herbert and Rackley) and the art referred to therein.

Lost, entangled, and abandoned fishlines are becoming major marine contaminants in the world's oceans, lakes and streams. As synthetic polymers have become the material of choice for such lines (due to their combination of strength and flexibility as well as their retention of these properties in use), more of these materials have accumulated, especially in heavily-fished waters. Snags and tangles of broken fishline products, including nets, are a growing hazard for entrapping fish, ducks and other wildlife. Many attempts have been made to overcome this problem without a satisfactory solution, hitherto.

We have analyzed past attempts, and have noted that many have attempted to develop degradable fishlines by increasing the hydrolysis rate of the polymers used to make the lines. In our opinion, however, this approach has failed because success in making and using a polymer that hydrolyzes more rapidly tends to shorten the total useful lifetime of the line; hydrolysis tends to occur not only while the line is submerged in water but also continues on wet line stored on a reel or when moisture is absorbed from humid air.

The desirability of a fishline, especially for casting, baitfishing, trolling, jigging, etc., depends greatly on the balance of strength, bending flexibility and longitudinal stiffness. This is discussed to some extent in U.S. Pat. No. 4,584,240. Deterioration in properties, e.g., by hydrolysis, affects not only the strength of a line, but also the balance of properties.

SUMMARY OF THE INVENTION

This invention provides a fishline of a polymer that is preferentially degraded while immersed in fishable waters but that degrades much more slowly when not so immersed, i.e., during storage and when exposed to air, even under humid conditions. This combines an advantage in degradability when immersed, while better preserving useful properties when not immersed in water.

The invention is based on our concept of using the oxygen present in fishable waters (which are aerated, otherwise the fish could not survive) to oxidatively degrade the polymer of the fishline, especially those of segmented copolyetherester. We have been surprised to find that this occurs preferentially even when fishlines of selected compositions are immersed in aerated water vs. exposure to ambient air. We can increase this preferential degradation effect by adding to the fishline certain stabilizers, such as a water-extractable antioxidant, so the stabilizer can preserve the line during storage in air before use, but will allow the line to disintegrate faster after immersion. Clearly, it is not desirable, however, to include an antioxidant that prevents oxidative degradation of the polymer, and thus prevents disintegration of the fishline, when immersed.

Accordingly, our invention consists of a fishline made with a copolyester having copolymerized polyalkylene ether glycol units and, optionally, a suitable concentration of a stabilizer. Such stabilizers may be used to extend the useful lifetime of the line to a more desirable level, e.g., about a year in ambient air exposure, without excessively decreasing the disintegration time of line abandoned under water.

In order to provide adequate strength, a selection of copolyetheresters which respond to a process of two stage drawing to yield tensile strengths over 50,000 psi (50 Kpsi) is made. To provide an improved fishline by increasing the longitudinal stiffness of line, making it more responsive to movements imposed by the fisherman during jigging, trolling and hook setting, while preserving low flexural stiffness of the line which is advantageous in casting and rewinding the line, a co-extruded sheath/core structure may be provided in which the core is a minor amount of the fiber cross section and has a higher modulus than the predominant sheath.

Although the invention is more particularly described in relation to single lines, especially monofilamentary lines such as are described in the art already mentioned, it will be understood that the invention may also be applied to related products, such as fishing nets, for example, which may be of different structures, if desired.

DETAILED DESCRIPTION OF PREFERRED EMBODIMENTS

Accordingly, such a preferred aerated-water-degradable fishline according to the invention comprises a copolyester monofilament consisting essentially of recurring structural units of the formula:

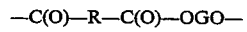

wherein R is 75 to 100 mole% T (para-phenylene), any remainder being another divalent hydrocarbylene radical, including aromatic radicals, aliphatic and cycloaliphatic radicals, such as are disclosed in copending U.S. Pat. No. 5,097,004 and copending U.S. Patent Applications Nos. 07/834,796 and 07/834,794, and wherein G is at least about 5% by weight of a radical of a polyalkylene ether glycol of MW at least 250, with, optionally, up to 10 mole % of a polyethylene ether radical selected from the group consisting of —(CH$_2$)$_2$—O—(CH$_2$)$_2$— and —(CH$_2$)$_2$—O—(CH$_2$)$_2$—O—(CH$_2$)$_2$—, respectively, DEG and TEG, and with the remainder being selected from the group consisting of C$_2$–C$_4$ lower alkylene groups, such as 2G (ethylene) and 4G (tetramethylene).

The polyalkylene ether glycol is preferably polytetramethylene ether glycol or polyethylene ether glycol with molecular weight of 250 to 6000.

Optionally, up to about 3 mole %, e.g., about 0.1 to 3 mole % of an alkali metal or alkaline earth metal sulfonated comonomer may be present, with preferred amounts being 1 to 2.5 mole %.

Optionally, a branching monomer may be present in amount less than 0.3 mole%.

Preferably the fishline is a copolyester from terephthalic acid and ethylene or tetramethylene glycol and 10 to 30 wt% polyalkylene ether radicals, and optionally 0.1 to 3 mole % sulfonated diacid, and 0 to 5 mole % diethylene glycol, and containing 2 to 2000 ppm of water-extractable stabilizers.

Optionally, one or more suitable stabilizers may be present in amount up to 5 % by weight. Suitable stabilizers may be mixtures of water-extractable antioxidants, such as hindered phenols, UV screeners such as substituted benzotriazole or benzophenones, and hindered amine light stabilizers. Desirably, the fishing line should completely disintegrate when left in water for a period of 1 year or less. In practice, a suitably shortened test period for preferred fish lines may be 2 months, within which period the fishline should desirably lose at least about 15% of its initial tensile strength when immersed in aerated water at 30 C., but should desirably retain at least about 95% (i.e., not lose more than about 5%) of its initial tensile strength when stored in ambient air in the dark, i.e., protected from light. An antioxidant that we have used in Example 1 according to the invention is 1,6-hexamethylene bis-(3,5-di-tert-butyl-4hydroxyhydrocinnamate) (Irganox 259 from Ciba Corporation). In contrast, the use of antioxidants that prevent degradation more effectively in water, such as N,N'-hexamethylene bis-(3,5-di-tert-butyl-4-hydroxyhydrocinnamide ) and N,N'-trimethylene bis-(3,5-di-tert-butyl-4-hydroxy-hydrocinnamide), is reported at the end of Example 2. Antioxidants that are readily extracted in water are expected to be useful in the practice of the invention. Desirably, light stabilizers are included, and are preferably less rapidly extracted than the antioxidants.

A route to provide a monofilament fishing line which has outstanding hook setting performance and feel as well as excellent castability is discussed in U.S. Pat. No. 4,584,240, which is incorporated herein by reference, as is U.S. Pat. No. 2,932,482. By adding a core with a higher tensile modulus than the sheath, it is possible to improve the hook setting performance of a line without detracting from its castability. For example, in the present invention, the hook setting performance of the line may be improved by adding a core composed of a blend of, by weight, approximately 80% of a degradable copolyester and 20% of the polymer used in Example 2A herein, where the core would comprise approximately 10% of the cross section. This core copolyester may be, for example, one or more of the compositions covered in U.S. Pat. Nos. 5,053,482, 5,097,004, 5,097,005 and in Application Ser. No. 07/834,794. Indeed, it may prove desirable to provide a small core of a less degradable polymer, if, for example, its small size (and low strength) will mean that the core will disintegrate sufficiently fast or will not pose a residual significant contaminant in the water for other reasons.

It will be noted that the abbreviations used herein are the same as used in the foregoing patents, the disclosures of which are hereby incorporated herein, by reference.

Such coextruded fishing lines desirably have a wet tensile strength of at least 50 Kpsi, and especially a tensile strength greater than 70 Kpsi and use a core polymer or polymer blend selected such that the wet initial tensile modulus of the core is significantly greater than the wet initial tensile modulus of the sheath.

Those skilled in the art will also be able to apply this technique to other constructions without departing from the spirit of the invention. An example of such application would include lines having a sheath and core construction with more than two layers of polymer. Another example is netting products of lines such as referred to above, and such as can be prepared from filaments of the indicated polyesters by known techniques.

TEST METHODS

Before tensile testing, the monofilaments should be (and were, when tested as herein described) allowed to equilibrate by storage in a conditioned environment (approximately 23 C. and 50 or 65% relative humidity. for at least 16 hours or by soaking in water maintained at approximately 23 C. for at least 16 hours).

A recording stress-strain device is used wherein a straight 10 inch long section of monofilament is elongated at the rate of 10 inches per minute until it breaks. With samples which were not available in 10 inch lengths, a 1 inch length was used, and was elongated at a rate of 1 inch per minute. Tensile strength is calculated by dividing the breaking load in pounds by the cross-sectional area of the monofilament in square inches.

Storage in ambient air is considered herein to be storage under controlled laboratory conditions at 23 degrees C. and 50% RH, and the materials should be stored in the dark, i.e., protected from light, unless otherwise indicated.

Aerated water exposure is considered herein to be exposure to aerated water (oxygen content 6–8 ppm) at 30 degrees C. while in the dark, i.e., protected from light, with a water exchange rate at about 20 liters of water per gram of exposed material per day, unless otherwise indicated.

The following Examples further illustrate the invention. Parts and percentages are by weight unless otherwise indicated. The components of the polyesters are, however, indicated as mole%, using the abbreviations indicated in the patents referred to herein.

EXAMPLE 1

This Example describes the preparation of a polymer, and its spinning and drawing to a monofilament, i.e., a fish line, and properties thereof, of composition 2G/DEG/PEG(600)(89/5/6)-T/55I (98/2) with about 0.2 wt% trimethyl trimellitate (TMTM) branching agent. This polymer contained 15wt% polyethylene ether(600) radicals (PEG) with 0.15% Irganox 259 added with the PEG, so present during polymerization. Irganox 259 is a stabilizer (anti-oxidant) whose presence did not prevent more degradation occurring during immersion in water than during storage in air, as will be related.

The polymer was prepared in a 35 gallon reactor containing a stirrer, a nitrogen inlet and a distillation column. In the reactor were placed:

37920 grams dimethyl terephthalate (DMT)

23 133 grams ethylene glycol (2G)
1092 grams diethylene glycol (DEG)
6771 grams PEG (MW 600) containing 1% Irganox 259
1182 grams dimethyl Na 5-sulfoisophthalate (5SI)
90 grams trimethyl trimellitate (TMTM)
8.75 grams Na(OAc).3H$_2$O
39.3 grams Sb$_2$O$_3$
27.8 grams Mn(OAc)$_2$.4H$_2$O The temperature of the reactor was slowly increased and 12000 ml distillate collected between 155 and 213 C. A second distillate (5400 ml) was collected between 224–240 C. The resultant oligomer was transferred to a second vessel containing an agitator and vacuum capabilities. Then 19.3 g of 85% phosphoric acid was added to the material and the temperature raised to 276 C. and the maximum vacuum (0.6 mm Hg) was established over 90 minutes. After 2.5 hours at these conditions, the contents of the reactor were discharged through a ribbon die into a water quench. The ribbon was cut to flake and dried at 60 C. overnight in a vacuum tray dryer with a vacuum between 1 and 2 mm Hg and a nitrogen purge.

Dried flake of this polymer was extruded at a rate of about 2.5 cu in./min. at a melt temperature of 260 C. through a round spinnerette orifice having a diameter of 0.04 1 inches. The filament so formed was passed vertically downward through an air gap for 1 inch, quenched in a 12 C. water bath for a distance of 5.5 feet and passed to a feed roll having a surface speed of 75 feet per minute. The filament was then passed through a 19 in. long radiant heater which exposes the filament to a temperature of 300 C. The filament was passed to unheated first stage draw rolls having a surface speed of 475 feet per minute to stretch the filament 6.33×. After the first stage draw rolls, the filament was passed through radiant heaters, having a combined length of 110 inches, and exposing the filament to a temperature of 450 C., on to second set of unheated draw rolls running at a speed of 1150 feet per minute which stretched the filament an additional 2.42×. The filament was collected on a spool.

The filament was light brown with a substantially round, 15.1 mil diameter cross-section. It had a tensile strength of 65,100 psi and an elongation to break of 19.7% (50% RH).

After being soaked in 23 C water overnight, the filament had a lower tensile strength of 54,800 psi and an elongation to break of 24.7%.

After the filament was immersed in an 80 C. water bath for 53 days, it was brittle and it disintegrated into powder on handling. The Mn of the residual powder was 4750.

After storing this line on a spool under ambient conditions including exposure to indoor lighting for about 22 months, the T/E/M were 68.6 Kpsi/40 %/511 Kpsi (1 inch gage length, 65% RH). There was little change from its initial strength.

Four ~6 in. long pieces of the fish line were placed in a length of ¼ in. O.D. stainless steel tubing, one end of which had a screen with holes finer than the diameter of the line attached and 30 C. tap water containing dissolved air was fed through the other end at about 7–10 cc/min. The tube was immersed in a 30 C. water bath. After about 7 weeks of this exposure, the filaments were retrieved and found to have T/E/M=51.2 Kpsi/56%/312 Kpsi, (1 inch gage length, 65%RH), i.e., a 25% loss in strength.

EXAMPLE 2

This Example shows the preparation of fishlines (without stabilizer) from two segmented copolyether ester compositions (4G/PTMEG(1000)-T) and degradation of their strength in water, in contrast to their stability in air. The molar proportions of the glycols were 96/4 and 92/8, respectively, 4G/PTMEG(1000) for 2A and 2B, corresponding to 16% and 26% by weight, respectively, of the high molecular weight polyalkylene radicals.

The 2A polymer was prepared in a 35 gallon reactor containing a stirrer, a nitrogen inlet and a distillation column. In the reactor were placed:
34064 grams dimethyl terephthalate (DMT)
23133 grams 1,4 butane diol (4G)
7167 grams polytetramethylene ether glycol (MW 1000) (PTMEG)
136 grams tetrabutyl titanate
82 grams Na(OAc).3H$_2$O The temperature of the reactor was slowly increased. Distillate (10800 ml methanol) was collected between 136 and 194 C. The resultant oligomer was transferred to a second vessel containing an agitator and vacuum capabilities. The temperature was raised to 252 C. and the maximum vacuum (2.2 mm Hg) was established over 45 minutes. After 4.5 hours at these conditions, the contents of the reactor were discharged through a ribbon die into a water quench. The ribbon was cut to flake and dried at 100 C. for at least 8 hours in a Patterson Kelly double cone vacuum dryer with a vacuum less than 5 mm Hg and a nitrogen purge.

The 2B polymer was prepared similarly. In a 35 gallon reactor containing a stirrer, a nitrogen inlet and a distillation column were placed:
30209 grams dimethyl terephthalate (DMT)
204 11 grams 1,4 butane diol (4G)
11975 grams polytetramethylene ether glycol (MW 1000) (PTMEG)
136 grams tetrabutyl titanate
82 grams Na(OAc).3H$_2$O The temperature of the reactor was slowly increased. Distillate (10000 ml methanol) was collected between 139 and 196 C. The temperature was raised to 252 C. and the maximum vacuum (1.4 mm Hg) was established over 45 minutes. After 3.25 hours, the contents of the reactor were discharged through a ribbon die, quenched, flaked and dried as in 2A.

Dried flake of each polymer was extruded at a melt temperature of 215 degrees Celsius through a round spinnerette orifice having a diameter of 0.045 inches. The filament so formed was passed vertically downward through an air gap for 5 inches, quenched in a water bath at 30 degrees Celsius for a distance of 5.5 feet and passed to a feed roll having a surface speed of 90 feet per minute. The filament was then passed through a first stage radiant heater having a length of 4 inches and a temperature of 1000 deg C. After passing through the radiant heater, the filament was passed to unheated first stage draw rolls having a surface speed of 405 feet per minute (referred to in the Table below as 2nd rolls).

Between the feed roll and first stage draw rolls, the filament was stretched 4.5×. From the first stage rolls the filament was passed through a second stage radiant heater (having a combined length of 110 inches and a temperature of 250 degrees Celsius) to second stage draw rolls running at a speed of 639 feet per minute which stretched the filament an additional 1.58X (and are referred to as 3rd rolls in the Table below).

From the second stage draw rolls the filament was passed through radiant heaters having a total length of 84 inches and a temperature of 200 degrees Celsius and then to third stage rolls running at a speed of 607 feet per minute, which allowed the filament to shrink 5% (and are referred to as 4th rolls in the Table below). The filament was then wound onto a package.

Operating conditions for items 2A and 2B of the Example cases are summarized as follows:

|  | 2A | 2B |
|---|---|---|
| First roll (fpm) | 90 | 90 |
| 1st stage heater temperature (deg C.) | 1000 | 1000 |
| 2nd rolls (fpm) | 405 | 405 |
| 2nd stage heater temperature (deg C.) | 250 | 210 |
| 3rd rolls (fpm) | 639 | 639 |
| 3rd stage heater temperature (deg C.) | 200 | 200 |
| 4th rolls (fpm) | 607 | 607 |

The 2A line had T/E/M/diameter=89.7 Kpsi/25.6%/299 Kpsi/10.0 mils and the 2B line 63.1 Kpsi/28.3%/165 Kpsi/10.6 mils (10 inch gage length, 50% R.H.).

2–4 6 in. long pieces of fishline were placed in an ~1 ft long piece of ¼ inch OD, 0.065 inch wall thickness stainless steel tubing with a fitting holding a screen on one end. Tap water saturated with air and heated to 30 C. was passed through the tube at about 5–10 cc/min. The tube was immersed in a 30 C. water bath. After about 2 months the samples were removed and tested. The 2A line had T/E/M=35.7 Kpsi/108%/176 Kpsi: the 2B line had 16.4 Kpsi/56 %/94 Kpsi (1 inch gage length, 65% RH). Samples of the same lines which had been exposed to air but protected from light in an opaque plastic bag had T/E/M =87.3 Kpsi/54%/223 Kpsi and 60.5 Kpsi/66%/85 Kpsi. These results show 60 and 74 % losses in tensile strength, respectively, on exposure to flowing aerated water vs the original strength in contrast to only 3% and 4% losses from the original strength on shaded ambient air exposure. When not shielded from light, the strength reduction of 2A and 2B in air was markedly higher.

In contrast, the following comparative T/E/M measurements were obtained on different samples (not according to the invention) after immersion in water at 30 C. for 5 weeks, and on similar samples made at the same time, but exposed to ambient air instead of being immersed in water over that period:

|  | Ambient | | | Water (30 degrees C.) | | |
|---|---|---|---|---|---|---|
|  | T(Kpsi) | E(%) | M(Kpsi) | T(Kpsi) | E(%) | M(Kpsi) |
| A | 95.6 | 68 | 225 | 93.0 | 56 | 265 |
| B | 80.3 | 73 | 98 | 77.6 | 86 | 86 |

These results show relatively little more degradation in water than in air, over the 5 week testing period. The polymers used for "A" and "B" in this test were chemically similar to those for the 2A and 2B polymers, respectively, except that about 0.1% by weight of TMTM branching agent was used (see Example 1) and about 0.15% by weight each of N,N'-hexamethylene bis-(3,5-di-tert-butyl-4-hydroxy-hydrocinnamide), and N,N'-trimethylene bis-( 3,5-di-tert-butyl-4-hydroxy-hydrocinnamide).

EXAMPLE 3

This Example describes the preparation of unstabilised fishline from compositions like those in Example 2 except that 2 mole % Na 5-sulfoisophthalate (5SI) radicals were present in the copolyetheresters (98/2-T/5SI, instead of all T).

Polymer 3A was prepared similarly to 2A from:
  34064 grams dimethyl terephthalate (DMT)
  23587 grams 1,4 butane diol (4G)
  7167 grams polytetramethylene ether glycol (MW 1000) (PTMEG)
  136 grams tetrabutyl titanate
  82 grams Na(OAc).3H₂O
  1066 grams dimethyl Na 5-sulfoisophthalate (5 SI)

Distillate (10300 ml methanol) was collected between 146 and 193 C. The temperature was raised to 252 C. and the maximum vacuum (1.7 mm Hg) was established over 45 minutes. After 1.75 hours at these conditions, the contents of the reactor were discharged through a ribbon die, quenched, cut and dried.

Polymer 3B was prepared from:
  30209 grams dimethyl terephthalate
  204 11 grams 1,4 butane diol
  11975 grams polytetramethylene ether glycol (MW 1000) (PTMEG)
  136 grams tetrabutyl titanate
  82 grams Na(OAc).3H₂O
  953 grams dimethyl Na 5-sulfoisophthalate 8900 ml of methanol was collected between 145 and 192 C. The temperature was raised to 255 C. and the maximum vacuum (1.9 mm Hg) established over 45 minutes. After 2.4 hours the polymer was discharged and converted to dried flake as above.

The lines were made as described in Example 2 with the following variations in drawing conditions:

|  | 3A | 3B |
|---|---|---|
| First roll (fpm) | 90 | 90 |
| 1st stage heater temperature (deg C.) | 1000 | 1000 |
| 2nd rolls (fpm) | 405 | 405 |
| 2nd stage heater temperature (deg C.) | 210 | 210 |
| 3rd rolls (fpm) | 649 | 639 |
| 3rd stage heater temperature (deg C. | 200 | 200 |
| 4th rolls (fpm) | 615 | 607 |

The T/E/M/diameter of the 3A line was 84.5 Kpsi/22.2%/313 Kpsi/10.4 mils and that of the 3B line was 63.2 Kpsi/27.5%/175 Kpsi/10.4 mils After the 2 month exposure in water, as described in Example 2, the 3A line had T/E/M =66.5 Kpsi/48%/244 Kpsi and the 3B line 35.9 Kpsi/45%/120 Kpsi. The air exposed samples had T/E/M =83.2 Kpsi/50%/234 Kpsi and 65.3 Kpsi/61%/91 Kpsi. Thus, there were 21% and 43% losses, respectively, in tensile strength on water exposure vs the original strength, in contrast to only a 2% loss and a 3% gain, respectively, after shaded ambient air exposure vs the original strength.

We claim:

1. A degradable fishing line that consists essentially of a monofilament having a tensile strength of at least 50,000 psi, said monofilament consisting essentially of a linear polyester consisting essentially of recurring structural units of the formula:

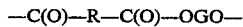

wherein R consists essentially of divalent hydrocarbylene radicals and at least 75 mole % of R is p-phenylene,
wherein G consists essentially of the following radicals:
a radical of a polyalkylene ether glycol of molecular weight at least 250, in amount at least 5 % by weight of the polyester,
a polyethylene ether radical selected from the group consisting of —(CH$_2$)$_2$—O—(CH$_2$)$_2$—and —(CH$_2$)$_2$—O—(CH$_2$)$_2$—O—(CH$_2$)$_2$—, in amount up to about mole % of G,
and the remainder of G is a hydrocarbylene radical selected from the group consisting of

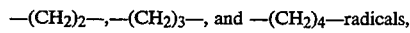

and wherein up to 3 mole % of the polyester may contain alkali metal or alkaline earth metal sulfo groups;
and wherein the polyester is stabilized by a stabilizer, in amount up to 5 percent by weight said stabilizer and said amount being, selected such that the tensile strength of the fishing line is not reduced more than 5 % over a 2 month storage period in ambient air, when protected from light, but is reduced by at least 15 % over a 2 month period of exposure to aerated water at 30 degrees C.

2. A degradable fishing line that consists essentially of a monofilament having a tensile strength of at least 50,000 psi, said monofilament consisting essentially of a linear polyester consisting essentially of recurring structural units of the formula:

wherein R consists essentially of divalent hydrocarbylene radicals and at least 75 mole % of R is p-phenylene,
wherein G consists essentially of the following radicals:
a radical of a polyalkylene ether glycol of molecular weight at least 250, in amount at least 5 % by weight of the polyester,
and the remainder of G is a hydrocarbylene radical selected from the group consisting of

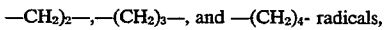

and wherein up to 3 mole % of the polyester may contain alkali metal or alkaline earth metal sulfo groups;
and wherein the polyester is stabilized by a stabilizer, in amount up to 5 percent by weight said stabilizer said amount being, selected such that the tensile strength of the fishing line is not reduced more than 5% over a 2 month storage period in ambient air, when protected from light, but is reduced by at least 15% over a 2 month period of exposure to aerated water at 30 degrees C.

3. A fishing line according to claim 1, wherein the polyester contains up to 0.3 mole % of a trifunctional branching agent.

4. A fishing line according to claim 2, wherein the polyester contains up to 0.3 mole % of a trifunctional branching agent.

5. A fishing line according to any one of claims 1 to 4, wherein the monofilament is composed of a core and a sheath of one or more concentric layers, said core having a significantly higher wet initial tensile modulus than said sheath that consists essentially of said polyester.

* * * * *